US010107713B2

(12) United States Patent
Spandl et al.

(10) Patent No.: US 10,107,713 B2
(45) Date of Patent: *Oct. 23, 2018

(54) LOW SPEED WIND TUNNEL DESIGN FOR AGRICULTURAL SPRAY PARTICLE ANALYSIS

(71) Applicant: WINFIELD SOLUTIONS, LLC, Shoreview, MN (US)

(72) Inventors: Eric P. Spandl, Shoreview, MN (US); Jon Martin Gehring, Hudson, WI (US); Gregory Keith Dahl, Eagan, MN (US); Joe V. Gednalske, River Falls, WI (US); William Thomas Hambleton, Hudson, WI (US); Lillian C. Magidow, St. Paul, MN (US)

(73) Assignee: WINFIELD SOLUTIONS, LLC, Shoreview, MN (US)

( * ) Notice: Subject to any disclaimer, the term of this patent is extended or adjusted under 35 U.S.C. 154(b) by 376 days.

This patent is subject to a terminal disclaimer.

(21) Appl. No.: 14/823,357

(22) Filed: Aug. 11, 2015

(65) Prior Publication Data

US 2015/0346052 A1    Dec. 3, 2015

Related U.S. Application Data

(63) Continuation of application No. 14/199,531, filed on Mar. 6, 2014, now Pat. No. 9,116,068, which is a
(Continued)

(51) Int. Cl.
*G01M 9/00* (2006.01)
*G01M 9/04* (2006.01)
*G01N 15/02* (2006.01)

(52) U.S. Cl.
CPC .............. *G01M 9/04* (2013.01); *G01N 15/02* (2013.01); *G01N 15/0205* (2013.01)

(58) Field of Classification Search
None
See application file for complete search history.

(56) References Cited

U.S. PATENT DOCUMENTS

| 2,592,322 A | 4/1952 | Nerad |
| 3,111,842 A | 11/1963 | Fredette et al. |
| (Continued) | | |

OTHER PUBLICATIONS

Reichard, D.L. et al., "Wind Tunnel Evaluation of a Computer Program to Model Spray Drift", Transactions of the ASAE, vol. 35(3): May-Jun. 1992, pp. 755-758.
(Continued)

*Primary Examiner* — Peter Macchiarolo
*Assistant Examiner* — Jermaine Jenkins
(74) *Attorney, Agent, or Firm* — Dorsey & Whitney LLP

(57) ABSTRACT

A wind tunnel device defines a cyclical tunnel to receive continuous airflow. Airflow is delivered through the tunnel to a testing region that includes a first portion carrying an arm including a spray tip configured to spray particulates in the testing region at an angle, and a second portion including an enlarged cutout region configured to receive the angled sprayed particulates. As airflow carries the angled spray particulates into the second portion, the enlarged cutout region enables the spray particulates to pass through and exit the second portion of the testing region. Analysis in the second region may be conducted through transparent walls free of openings to minimize exposure of the spray particulates to the exterior of the device. A scrubber is adapted to extract spray mist from the airflow as the airflow exits the testing region and is re-circulated through the cyclical tunnel.

19 Claims, 7 Drawing Sheets

Related U.S. Application Data continuation of application No. 13/614,522, filed on Sep. 13, 2012, now Pat. No. 8,689,619.

(60) Provisional application No. 61/588,058, filed on Jan. 18, 2012.

(56) References Cited

U.S. PATENT DOCUMENTS

| | | | |
|---|---|---|---|
| 3,456,503 A | 7/1969 | Wise | |
| 3,739,634 A | 6/1973 | Johnson et al. | |
| 4,033,185 A | 7/1977 | McNally et al. | |
| 4,648,267 A | 3/1987 | Seegmiller | |
| 5,186,046 A * | 2/1993 | Gouterman | G01L 11/02 374/143 |
| 5,942,682 A | 8/1999 | Ghetzler et al. | |
| 6,155,111 A * | 12/2000 | Wickern | G01M 9/04 73/147 |
| 6,997,049 B2 * | 2/2006 | Lacey, Jr. | G01M 9/02 257/E29.272 |
| 7,028,542 B2 * | 4/2006 | Metni | A63G 31/00 73/147 |
| 7,997,130 B1 * | 8/2011 | Stonner | G01M 9/04 73/147 |
| 8,650,944 B2 * | 2/2014 | Meis | F25C 1/00 73/118.03 |
| 8,656,769 B2 * | 2/2014 | Moliere | G01M 9/065 73/147 |
| 8,689,619 B2 | 4/2014 | Spandl et al. | |
| 9,116,068 B2 * | 8/2015 | Spandl | G01N 15/02 |
| 9,599,550 B2 * | 3/2017 | Van Der Mark | A61M 11/00 |
| 2005/0173561 A1 * | 8/2005 | Cotter | B05B 7/066 239/398 |
| 2012/0060536 A1 | 3/2012 | Ahonen et al. | |

OTHER PUBLICATIONS

Guler, H. et al., Wind Tunnel Evaluation of Drift Reduction Potential and Spray Characteristics with Drift Retardants at High Operating Pressure, Journal of ASTM International, vol. 3, No. 5, Paper ID JAI13527, pp. 1-9, available online at www.astm.org , published Feb. 17, 2006.

University of North Carolina, Applied Mathematics, "The Fluid Lab at Applied Mathematics", http://web.archive.org/web/20100612024021/ http://www.amath.unc.edu/lab/, date captured according to http://webarchive.org Jun. 12, 2010.

University of North Carolina, Applied Mathematics, "Tunnel Picture", http://www.amath.unc.edu/Faculty/rmm/tunnel.jpg May 22, 1999.

* cited by examiner

LOW SPEED WIND TUNNEL DESIGN FOR AGRICULTURAL SPRAY PARTICLE ANALYSIS

CROSS-REFERENCED RELATED APPLICATIONS

This application is a continuation of U.S. patent application Ser. No. 14/199,531 filed on Mar. 6, 2014, issued as U.S. Pat. No. 9,116,068 on Aug. 25, 2015, which is a continuation of U.S. patent application Ser. No. 13/614,522 filed on Sep. 13, 2012, issued as U.S. Pat. No. 8,689,619 on Apr. 4, 2014, which claims priority to U.S. Provisional Application No. 61/588,058 filed on Jan. 18, 2012, the entire contents of which are incorporated herein by reference.

FIELD OF THE INVENTION

This application relates to wind tunnel devices for agricultural spray analysis, and more particularly to wind tunnel devices configured as substantially closed systems that reduce exposure to agricultural sprays during analysis while providing for the aerodynamic flow of air and spray particulates.

BACKGROUND

Due to increasing concern about pest control costs and environmental pollution associated with agricultural sprays, application of such sprays requires precision and care. Considerable research on spray drift has been conducted, but it remains a major problem associated with many agricultural spray applications.

Field tests provide some information on factors influencing spray drift. However, field tests are limited by weather conditions that cannot be controlled and often vary during a test. Due to non-controlled environment, assessing the influence of some variables on spray drift is difficult. Consequently, laboratory tests are used to evaluate drift associated with spray deposits discharged from spray tips at various wind velocities in wind tunnels. However, wind tunnels are generally costly and may expose the tester to the agricultural spray, which can have negative health effects on the tester.

The US EPA will soon implement a new Drift Reduction Technology (DRT) program which would allow farmers and applicators to reduce the size of buffer zones required on some herbicide labels. DRT will need to be certified through the use of spray particle analysis or field trials proving a reduction in fine droplets subject to off-target drift. As a result, more frequent use of wind tunnels may be required for certification.

SUMMARY

In view of the foregoing, there is a need to provide wind tunnel devices that are configured cost-effectively and that shield operators of the wind tunnel devices from exposure to potentially harmful agricultural sprays. Accordingly, wind tunnel devices provided herein are configured as substantially enclosed systems for transporting airflow through the system to carry agricultural spray droplets past an analyzer, capturing substantially all of the spray droplets, and re-circulating the airflow through the system. The closed systems may have a rectangular shape and may include devices for facilitating an aerodynamic flow of the air through the system as well as transparent sidewalls free of openings adjacent to the analyzer.

According to one implementation, a wind tunnel device includes a segmented enclosure configured with an enclosed interior defining a cyclical tunnel for receiving continuous airflow therein. An airflow system delivers airflow through the tunnel including a testing region therein. In the testing region, a first portion carries an arm including a spray tip configured to spray particulates in the testing region at an angle and a second portion includes an enlarged cutout region configured to receive the angled spray particulates. The second portion with the enlarged cutout region accommodates the area covered by the angled spray particulates. The airflow carries the angled spray particulates from the spray tip into the enlarged cutout region such that the angled spray particulates pass through and exit the second portion of the testing region. As the airflow exits the testing region, it returns to the airflow system through the enclosed interior defining of the cyclical tunnel thereby re-circulating the airflow.

According to another implementation, a method of analyzing spray particulates in a wind tunnel involves providing a segmented enclosure configured with an enclosed interior defining a cyclical tunnel for receiving continuous airflow therein; providing an airflow system and a testing region within the segmented enclosure such that the airflow system delivers airflow through the cyclical tunnel including the testing region; providing the testing region with a first portion carrying an arm including a spray tip configured to spray particulates in the testing region at an angle and providing the testing region with a second portion including an enlarged cutout region for accommodating the area covered by the angled spray particulates and a transparent sidewall free of openings. Angled spray particulates are sprayed from the spray tip and are analyzed through the transparent sidewall free of openings. The airflow carries the angled spray particulates from the spray tip into the enlarged cutout region such that the spray particulates pass through and exit the second portion of the testing region. The airflow is re-circulated through the enclosed interior defining the cyclical tunnel as the airflow exits the testing region.

In yet a further implementation, a wind tunnel includes a fan, a first section, and second section, and a third section connected to form a generally rectangular shape, wherein the fan, the first section, the second section, and the third section form a tunnel that allows for the passage of air. A traversing arm is attached to the second section and adapted to receive a spray tip and to telescope and extend the spray tip into the volume defined by the second section. A first expansion cutout is attached the second section and forming a portion of a ceiling of the second section. A second expansion cutout is attached to the second portion and forming a portion of a floor of the second section. An angle of expansion of the first and second expansion cutouts enables spray particles from the spray tip to pass through and exit the second section.

DETAILED DESCRIPTION

Research has shown that the most reliable data for spray particle analysis comes from using a wind tunnel to move fine spray particles away from an analysis device to prevent duplicate measurements. This disclosure relates, in part, to low speed wind tunnels used for analysis of spray particle size.

Wind tunnel devices provided herein may provide for accurate laser analysis of spray particles, which may be used for: product development (such as spray tip development); formulation development (such as active ingredients, e.g., herbicides, and adjuvants, e.g., drift reducer compositions); product label development; drift reduction technology development (e.g., spray tips, active ingredients and adjuvants); and grower and applicator training and education. Wind tunnel devices may accordingly be configured to test a variety of herbicide active ingredients, adjuvants, spray tips, and combinations of these to evaluate potential off-target movement.

Figure 1:
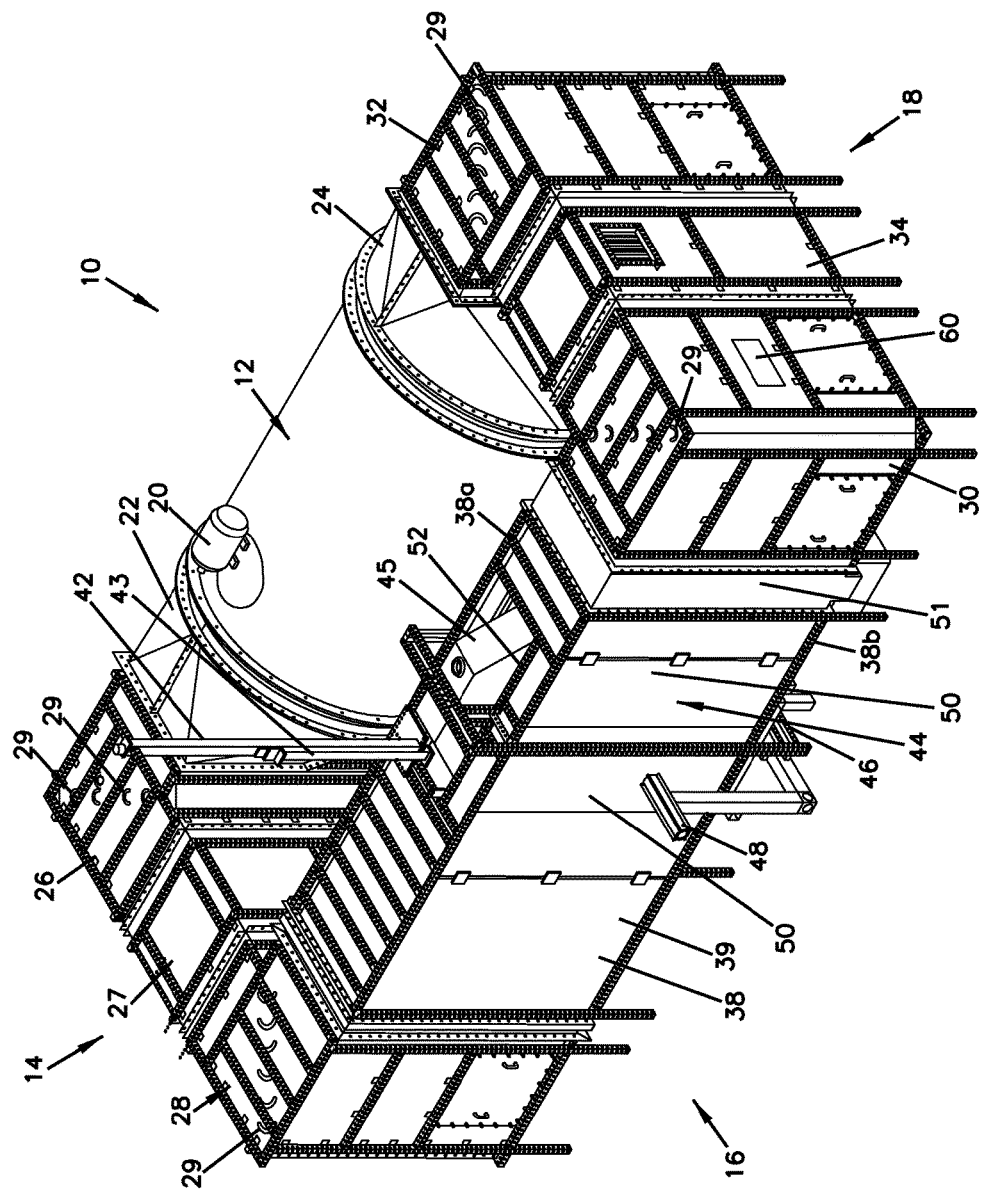
FIG. 1 shows a perspective view of one embodiment of a wind tunnel device according to certain implementations.

FIG. 1 shows a perspective view of one embodiment of a wind tunnel device 10 according to certain implementations. The wind tunnel device 10 may include a series of segments or sections. Each of the sections may include a first end and a second end, such as a ceiling and a floor, respectively, as well as sidewalls therebetween. The sections may be generally rectangularly shaped and open at two sides to enable the sections to be interconnected. Some of the sections may be configured as corners and may include two open sides arranged at a right angle. For example, as shown in FIG. 1, the wind tunnel device 10 may include a fan 12, a first section 14, a second section 16, and a third section 18. The fan 12 and the three sections 14, 16, 18 may form a generally rectangular footprint for containing the airflow. A tunnel 19 may be defined within the volume enclosed within an interior defined by the fan 12 and the three sections 14, 16, and 18 of the wind tunnel device 10 and may enable airflow to pass therethrough. The tunnel 19 may be cyclical such that a volume of airflow moves from the fan 12 sequentially into the sections 14, 16, 18, and from section 18, the airflow may re-circulate back into the fan 12 without allowing the passage of particulates or airflow to the exterior of the device. Providing a cyclical circuit enables the airflow to be reused, which reduces the amount of air exiting the wind tunnel device 10 and minimizes particulate exposure. In some implementations, seals may be provided between the sections to further minimize the possibility that particulates or circulating airflow will be transported outside the wind tunnel device 10.

Figure 5:
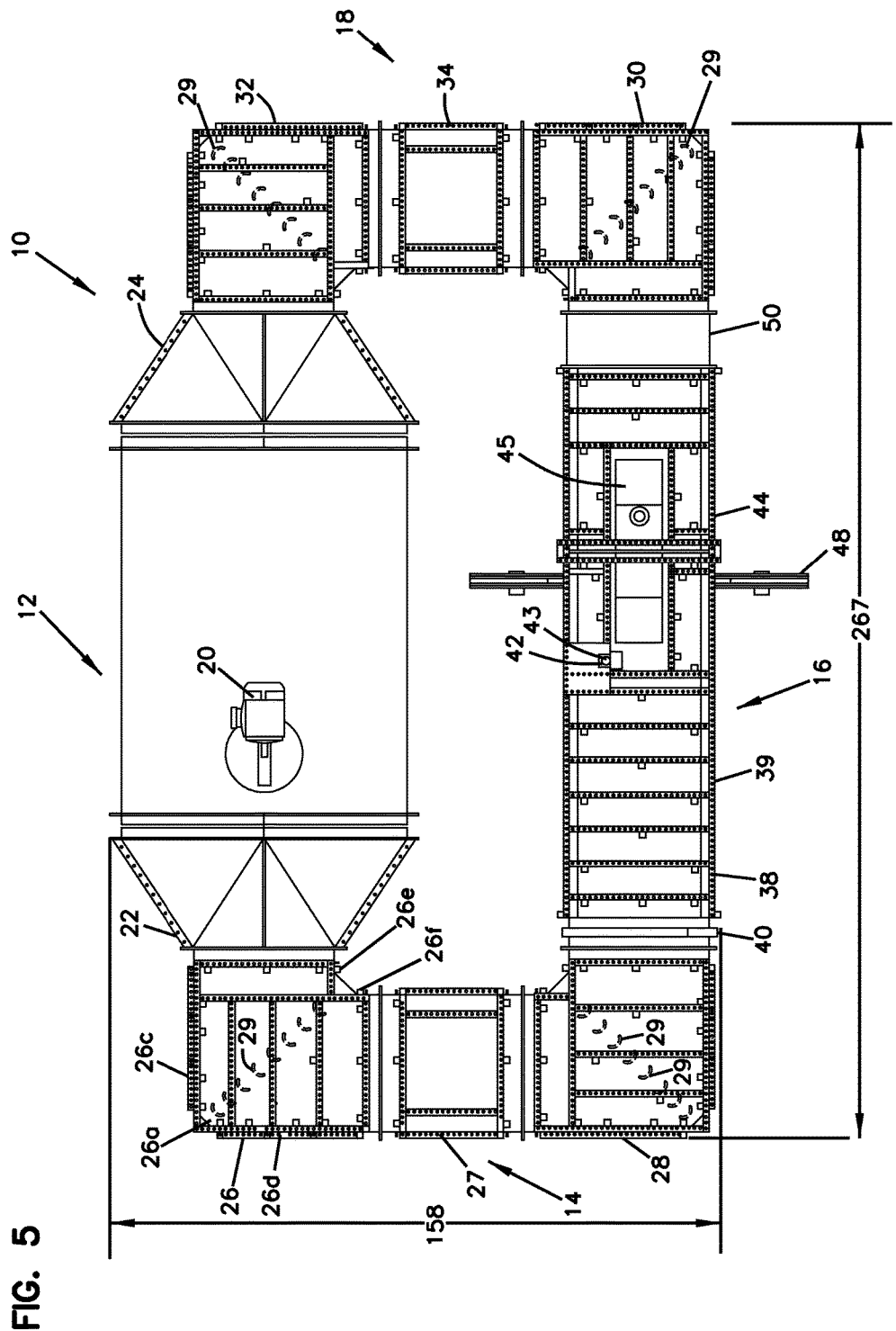
FIG. 5 is a top plan view of the wind tunnel device of FIG. 1.

The fan 12 of the wind tunnel device 10 may include a motor 20 configured to drive the fan 12, which may be communicatively coupled to a control system or an operating console of the wind tunnel device 10 (see FIG. 8). In a particular embodiment, the fan 12 is manufactured by Twin City Fan M/N (TSL SW Model 542), and is of the inline centrifugal type. As shown in FIGS. 1 and 5, the fan 12 may be joined to the first section 14 by a first duct 22 and to the third section 18 by a second duct 24. In one embodiment, the motor 20 is a 7.5 horsepower motor that may be configured to generate wind speeds of between about 1 and 20 miles per hour at a spray tip 25 (described below), or between about 1 and 14 miles per hour. Those skilled in the art will appreciate that a wide variety of commercially available fans with horsepower requirements ranging from 5 horsepower to 30 horsepower, or at about 5, 7.5, 10, 15, 20, 25, 30 horsepower may be used in connection with the wind tunnel device 10. Typically, the wind speed in the other portions of the flow circuit defined by the wind tunnel device 10 is equal to that of the test section, which is described further below in connection with the second section 12. However, in some implementations, flow may be expanded through a portion of the flow circuit and may be contracted through a duct or other air flow control device upstream from the test section.

Figure 2:
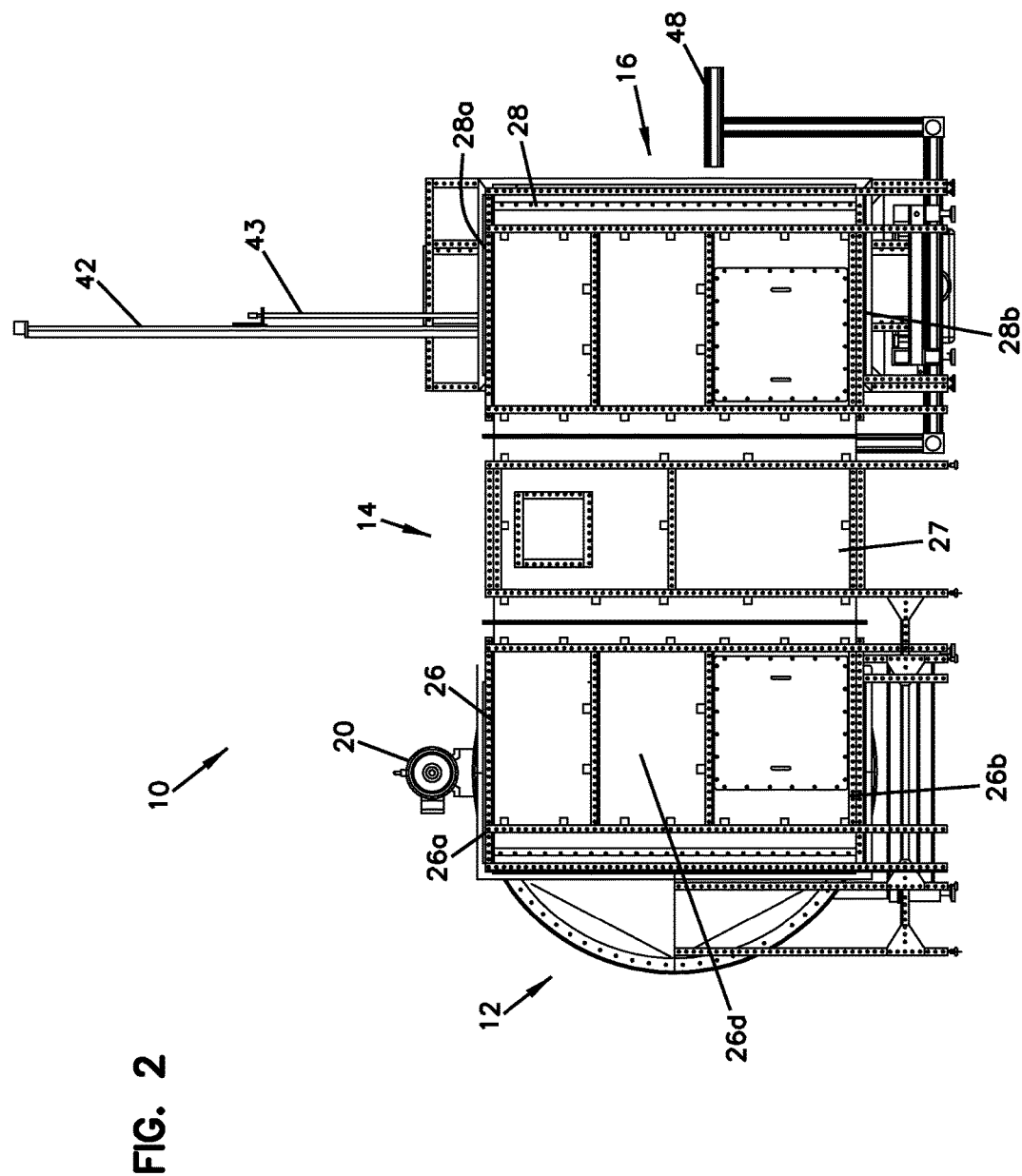
FIG. 2 shows a left side view of the wind tunnel device of FIG. 1.

The first section 14 of the wind tunnel device 10 may include a first corner 26, a first middle section 27 and second corner 28. As shown in FIGS. 1, 2 and 5, the first corner 26 may be joined to the second corner 28 by way of the first middle section 27 and may form one side of the generally rectangular shape of the wind tunnel device 10. A portion of the tunnel 19 is formed within the volume enclosed by the first section 14. As shown in FIGS. 1, 2, 3 and 5, each corner 26, 28 is generally rectangular, may define a generally rectangular cross-section and may define openings at right angles relative to one another. As shown in FIG. 5, two adjacent sides of a corner 26, 28 form a generally right angled surface at the exterior of the wind tunnel device 10. In order to limit wind resistance due to such angles, each of the first and second corners 26 and 28 may include turning vanes 29 within an interior of the corners 26, 28. The turning vanes 29 may be configured as vertically extending members joined to top ends 26a, 28a and bottom ends 26b, 28b of the first and second corners 26 and 28, respectively. In some implementations, the turning vanes 29 may be configured as louvers or aerodynamic arcuately shaped vanes. In more specific implementations, the turning vanes 29 may be constant-arc vanes (e.g., high efficiency profile (HEP) turning vanes manufactured by Aerodyne). Other turning vane geometries may include, but are not limited to, single thickness circular arc designs, multiple thickness circular arc designs, single thickness airfoil designs, and multiple thickness airfoil designs. In some implementations, the turning vanes 29 may be spaced intermittently along a diagonal line from the interior of the corner to the exterior of the corner 26, for example, extending between internal intersection points where the outside exterior walls 26c, 26d meet and at which internal exterior walls 26e, 26f meet. The turning vanes 29 may be configured to provide minimum loss and disturbance of air flow as the air turns the corner channels. That is, the turning vanes 29 may be placed at generally right angled surfaces within the corners 26, 28 to reduce wind resistance and direct airflow away from the right angled surfaces and some turning vanes 29 may be spaced apart within the corner 26, 28 to more evenly direct the airflow. In some implementations, airflow may be turned within the wind tunnel device without any turning vanes.

As shown in FIGS. 1, 3, 5 and 6, the second section 16 of the wind tunnel device 10 may be configured as a generally rectangular cabinet and may define the test section 38. The test section 38 may join to the second corner 28 of the first section 14 and to a first corner 30 of the third section 18. A portion of the tunnel 19 is formed within the volume enclosed by the test section 38.

The test section 38 of the second section 16 may generally define another side of the rectangular shape of the wind tunnel device 10. The rectangular test section 38 may be configured to include a first portion 39 with a honeycomb air stabilizer unit 40 (not shown), a traversing arm housing 42 with a traversing arm 43 holding the spray tip 25 (FIG. 6), a second portion 44 with a first expansion cutout 45, a second expansion cutout 46, a laser mount 48 that may hold a laser 49, glass wall sections 50 and a spray particle scrubber 51. The test section 38 may have an area that is 6 feet high by 3 feet wide by 12 feet long. In some implementations, the test section 38 may have various dimensions, and preferably the test section includes a length of at least 36 inches, and a width and a height that are at least one meter.

The first portion 39 of the test section 38 may be configured to accommodate movement of the traversing arm 43, described below. In addition, the first portion 39 may generally define a rectangular cross section with a ceiling at the upper end 38a of the test section 38, a floor at the lower end 38b of the test section 38, and a pair of opposing sidewalls arranged therebetween. In some implementations, glass wall sections 50 may be provided as the sidewalls of the first portion 39.

The honeycomb stabilizer unit 40 may generally be placed at the entrance to the test section 38. For example, the honeycomb stabilizer unit 40 may generally be positioned at the interface where the second corner 28 of the first portion 14 joins to the rectangular test section 38. The unit may include a honeycomb structure that allows air to pass through the structure, and may facilitate a more uniform and straight air flow from the second corner 28 into the test section 38. In one embodiment, the air stabilizer unit, or flow conditioner, may ensure both straightness and uniformity of the airflow as it passes the spray tip. The honeycomb stabilizer unit 40 may have a size and shape similar or the same as a cross-section of the wind tunnel, and may include a honeycomb structure with cells of various configurations. For example, a series of hexagonally-configured cells may each have dimensions of about 2 inches by about 0.25 inches. In addition to the hexagonal cell geometry, the cells may have square and round geometries, and may include cells sizes adapted for flow conditioning that may include a thicknesses likely ranging between 1" up to 4"×¼", ⅜", ½", ¾" and 1". Materials that may be used to fabricate the cells may include, but are not limited to, aluminum, polycarbonate, PVC, ABS, polypropylene, stainless steel, and titanium.

Figure 3:
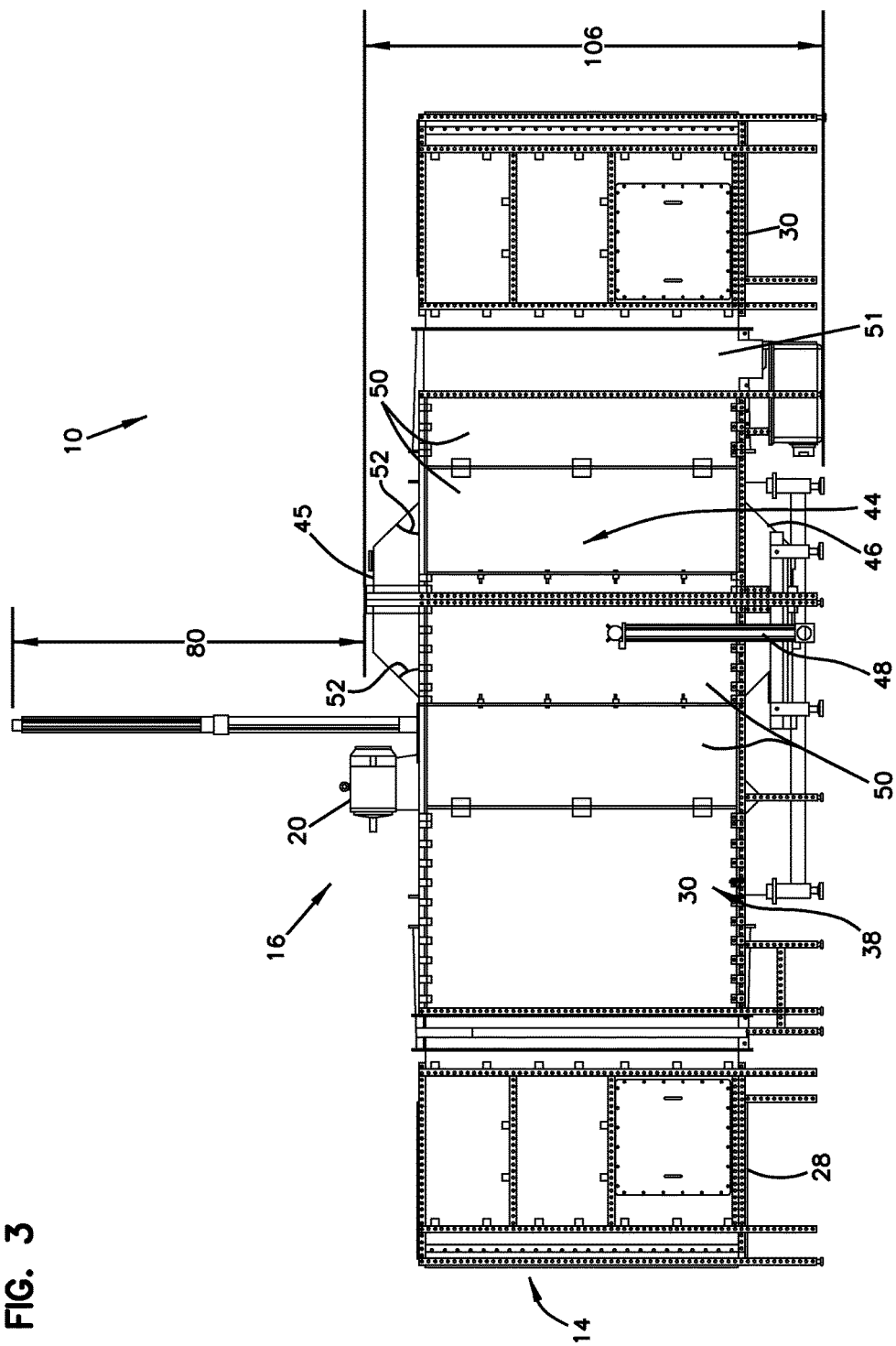
FIG. 3 is a front view of the wind tunnel device of FIG. 1.

The traversing arm housing 42 may be joined at the first portion 39 at a first end 38a of the test section 38, as shown in FIGS. 1 and 3. The traversing arm housing 42 may be configured to guide the traversing arm 43 into the space defined by the first portion 39 of the test section 38. In some implementations, the traversing arm housing 42 may include a track for guiding the traversing arm 43 and a seal arranged at an opening where the traversing arm 43 enters the test section 38. The seal between the housing 42 and the traversing arm 43 ensures spray particulates do not escape the test section during spraying and testing.

The traversing arm 43 may extend from the traversing arm housing 42 and may receive the spray tip 25. In some implementations, the spray tip 25 is offset from the traversing arm 43, for example by about 6 to 8 inches. In this example, the spray tip 25 may be coupled to the traversing arm 43 via a conduit such as a rigid conduit projecting horizontally from the traversing arm 43 and fluidly coupled to the spray tip 25. In further implementations, the traversing arm 43 or the conduit is adapted for the interchangeable attachment of spray tips and may include a supply line coupled to a fluid delivery system for delivering fluid to the one or more spray tips joined thereto. The spray tip 25 may be configured to emit a spray forming spray particulates, and the spray tip 25 may be selected from a variety of spray tips (e.g., nozzles) such as those used in agricultural applications.

The traversing arm 43 may be controllably lowered and raised between the first end 38a of the test section 38, which may be proximate a ceiling of the first portion 39 of the test section 38, and a second end 38b of the test section 38, which may be proximate a floor of the first portion 39. This movement may be through the use of a stepper motor (not shown), which moves the traversing arm 43 along the traversing arm housing 42.

Figure 6:
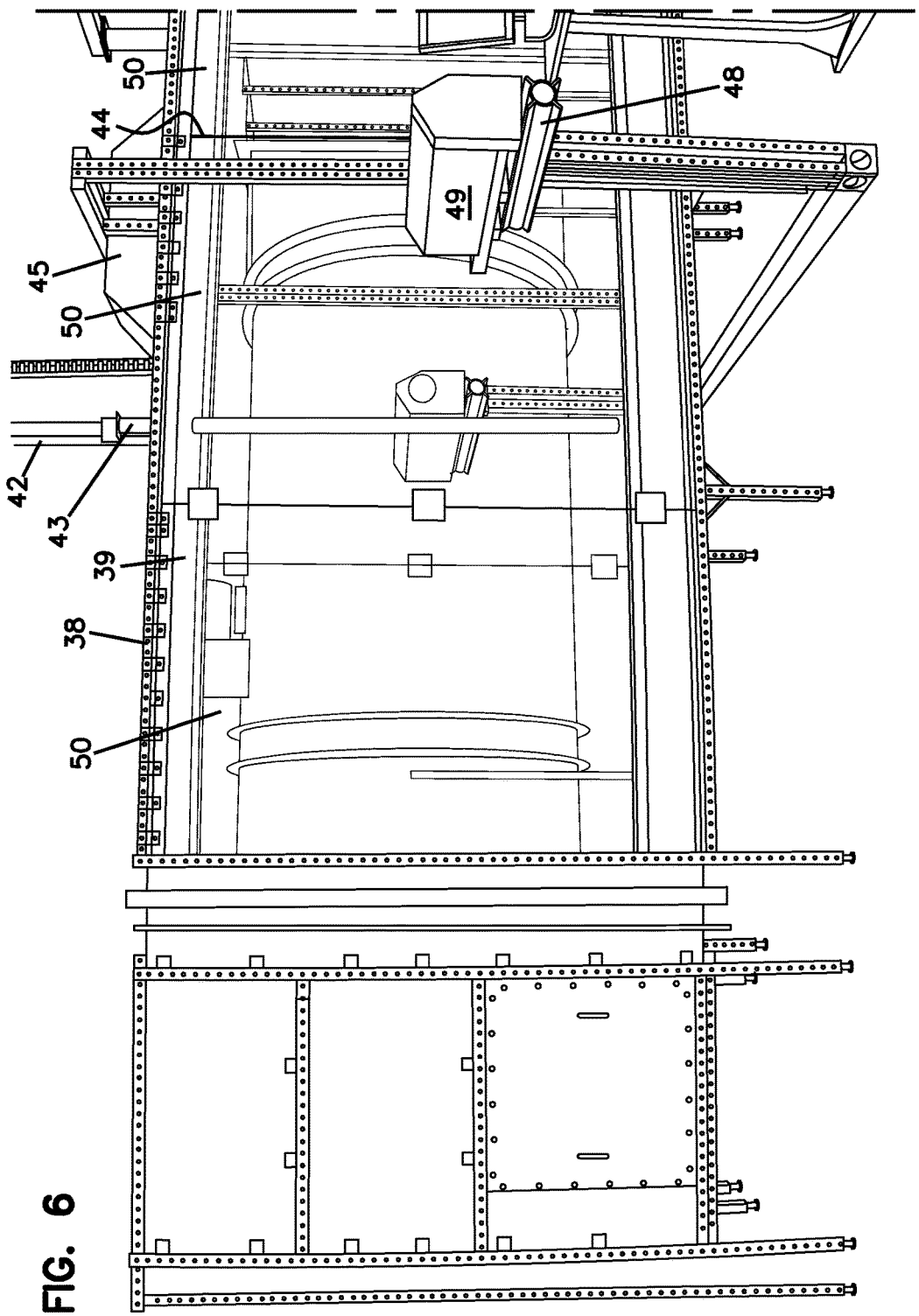
FIG. 6 is a front left side view of the wind tunnel device of FIG. 1.

In some implementations, the traversing arm 43 may be shaped similar to an airplane wing as shown in FIG. 6. For example, an airfoil shaped traversing arm 43 produced by Carlson Aircraft. Some suitable airfoil shapes for the arm 43 may be symmetrical circular arc shapes, symmetrical polynomial generated shapes, symmetrical matched ellipse shapes, and symmetrical NACA (National Advisory Committee for Aeronautics) airfoil shapes. The airfoil shape of the traversing arm 43 may provide less disruption to the air flow within the test section 38. However, other shapes may also be used for the traversing arm 43. In further implementations, the traversing arm housing 42 and traversing arm 43 may be fully enclosed within the test section 38. In this implementation, the traversing arm 43 may move along the traversing arm housing 42 within the test section 38, which may further minimize the possibility that particulates from the spray tip 25 will be transported outside the wind tunnel device 10.

The second portion 44 of the test section 38 may be configured as a fully enclosed testing region of the test section 38 where the spray particulates are analyzed. The second portion 44 includes a first expansion cutout 45 and a second expansion cutout 46 protruding outwardly from the first and second ends 38a, 38b of the test section 38 proximate a floor and a ceiling of the test section 38, respectively. The second portion 44 of the test section 38 with the expansion cutouts 45, 46 accordingly defines a space with cutouts forming an angled ceiling and an angled floor separated by sidewalls. The sidewalls of the second portion 44 may include the glass wall sections 50 in an area proximate where the spray analysis is conducted, described below. The configuration of the second portion 44 of the test section 38 accommodates the spray angles provided by the spray tip 25 joined to the traversing arm 43. In contrast, the space defined by the first portion 39 of the test section 38 may be unable to accommodate the spray angles provided by the spray tips 25 due to height limitations. For example, because the first portion 39 of the test section 38 is configured to allow the traversing arm 43 to translate between the first and second ends 38a, 38b of the test section 38, angled spray emitted from the spray tip 25 may otherwise contact the first and second ends 38a, 38b of the cabinet 30, e.g., the first portion 39 may define an area that is smaller than an area covered by the angled spray particulates. The expansion cutouts 45, 46 downstream from the spray tips 25 are configured to minimize such contact by the spray particulates.

The expansion cutouts 45, 46 may be configured as a five wall expansion piece with an opening for positioning over an opening in an upper or lower end 38a, 38b of the test section 38. Walls of the expansion cutouts 45, 46 include angled sides that define an expansion angle 52 that is approximately equal to the widest spray angle emitted by the spray tip 25 used in connection with the traversing arm 43. In some implementations the spray tip 25 may deliver a maximum spray angle of 140° and the expansion cutouts 45, 46 may be configured to accommodate this or other maximum spray angles. In some implementations, the expansion angle for the cutout may be about 45°. However, the expansion angle may vary from about 10° to about 90°. The depth of the expansion cutouts may be about 12 inches, and the size of the rectangles cut into the test section wall for receiving the expansion cutout may be about 12 wide by about 48 inches long. In some implementations, the cutouts 45, 46 may be configured with the same shape. The first expansion cutout 45 may include a drip tray that prevents any spray that impinges on the test section walls from dripping through the measurement area. The second expansion cutout 46 may include a drain for draining the collected liquid. In some implementations, the first expansion cutout 45 may define a small opening that may generally be capped, which may allow for a suction system to condition the flow past the first expansion cutout 45, for example.

The expansion cutouts 45 and 46 in combination with the second portion 44 of the test section 38 may be configured to allow the spray from wide and narrow angle spray tips 25 to be analyzed within the second portion 44 of the test section 38 without the spray bouncing off or collecting and dripping from the ceiling and the floor of the test section 38. For example, as a wide angle spray tip 25 is spraying a fluid (e.g., a herbicide) when it is at the top end 38a of the test section 38, the spray pattern of the herbicide may follow one or both of the angled expansion cutouts 45, 46 and the spray pattern may be allowed to flow along the expansion cutouts 45, 46 and the second portion 44 so that the spray pattern may be analyzed by the laser 48 and the particulates may exit the second portion 44. For example, the configuration of the expansion cutout 45 may prevent some droplets from forming on the ceiling of the first end 38a of the test section 38 above the space covered by the laser 49 by allowing the droplets to pass into and out of the expansion cutout 45. Similarly, the expansion cutout 46 may be configured at an angle at the second end 38b of the test section 38 to prevent splatter from the herbicide hitting the floor of the second end 38b of the test section 38 and enter the space covered by the laser 49 by allowing the droplets to pass into and out of the expansion cutout 46. The expansion cutouts 45, 46 may thus be configured to limit measurement errors due to errant drops (e.g., droplets that drip down from walls or bounce off of walls) passing through the laser path such as preventing fluid drops from forming as a result of hitting the ceiling or floor of the top and bottom ends 38a, 38b of the test section 38 and entering the space covered by the laser 49. Further, while some particulates may contact the drip tray of the first expansion cutout 45, the drip tray may prevent drop formation and channel the particulates downstream from the testing region thereby preventing such drops from falling in the space covered by the laser. Other particulates contacting the second expansion cutout 46 may be collected and drained.

The laser mount 48 of the test section 38 may be positioned proximate the second portion 44 of the test section 38 and may be configured to receive a laser 49 or other analysis devices. The laser mount 48 may be movable horizontally and/or vertically at least along the glass sections 50 of the second portion 44 to enable the laser 49 to measure spray particulates from various types of spray tips. For example, some spray tips 25 may deliver a sheet of liquid from an orifice and the sheet may break apart into spray particulates at a certain distance away from the orifice of the spray tips 25. In this example, the laser mount 48 and the laser 49 may be moved horizontally to a position along the second portion 44 corresponding to a location downstream from the nozzle where the spray particulates form. In some implementations, the laser mount 48 may translate horizontally from 0 to 24 inches from the spray tip, 2 to 18 inches from the spray tip or any combination thereof. In some implementations, the laser mount 48 may translate vertically while the spray tips remain stationary. While the analysis device described herein is a laser, it will be appreciated that other analysis devices may be used such as video imaging.

The glass sections 50 of the test section 38 may be configured to enable analysis, such as laser analysis, of the spray particulates without forming openings within the sidewalls of the test section 38. The glass used in the wind tunnel device 10 may be a ⅜" nominal thickness, low-iron, annealed, soda-lime glass. Acceptable glass configurations for the test section may include, but are not limited to, ¼" nominal thickness, ⅜" nominal thickness, and ¾" nominal thickness, and substantially equivalent metric sized materials. Acceptable compositions for the glass may include, but are not limited to, soda-lime, low-iron soda lime, and borosilicate. In some implementations, fused quartz and sapphire may be used in areas to where the laser analysis takes place. Low iron glass may be preferred due to its increased optical transmission. In addition, available tempers are annealed, strengthened, and tempered, but annealed glass is preferable due to its low optical distortion for the laser. Some installations may use tempered glass, for example, as a safety precaution. By analyzing the spray particulates within an environment separate from the user and from the analysis device, analysis may be performed by the user without risking exposure to potentially harmful chemicals and the analysis device remains free of spray particulates, which may facilitate avoiding inaccurate measurements. While providing glass sections 50 along sidewalls of the second portion 44 of the test section 38 is preferred, other areas of the test section 38 may also include glass sections. For example, as shown in FIG. 6, the first portion 39 of the test section 38 may include sidewalls formed of glass sections 50 such as optical glass walls configured to enable the user to view movement of the traversing arm 43. In some implementations, the glass sections 50 may be hinged to allow access to the interior of the test section 38, for example, to allow attachment of spray tips 25 and maintenance.

A spray particle scrubber 51 of the test section 38 may be joined between the second portion 44 of the test section 38 and the third corner 30 of the third section 18. In some implementations, the spray particle scrubber 51 may be configured to collect the droplets exiting the second portion 44 of the test section 38 and may prevent the droplets from continuing through the tunnel 19 defined by the wind tunnel device 10. With the use of a spray particle scrubber 51, the air may be reused and provided to the fan 12, for example. In one embodiment, the scrubber 51 may be configured as a mist extractor. In another embodiment, the scrubber 51 may be 99.7% effective at removing particles greater than 5 µm diameter. For example, the spray particle scrubber 51 may use a series of angled channels to change the flow path of the particles, allowing them to settle out and run down the channels, into the waste disposal unit.

Figure 7:
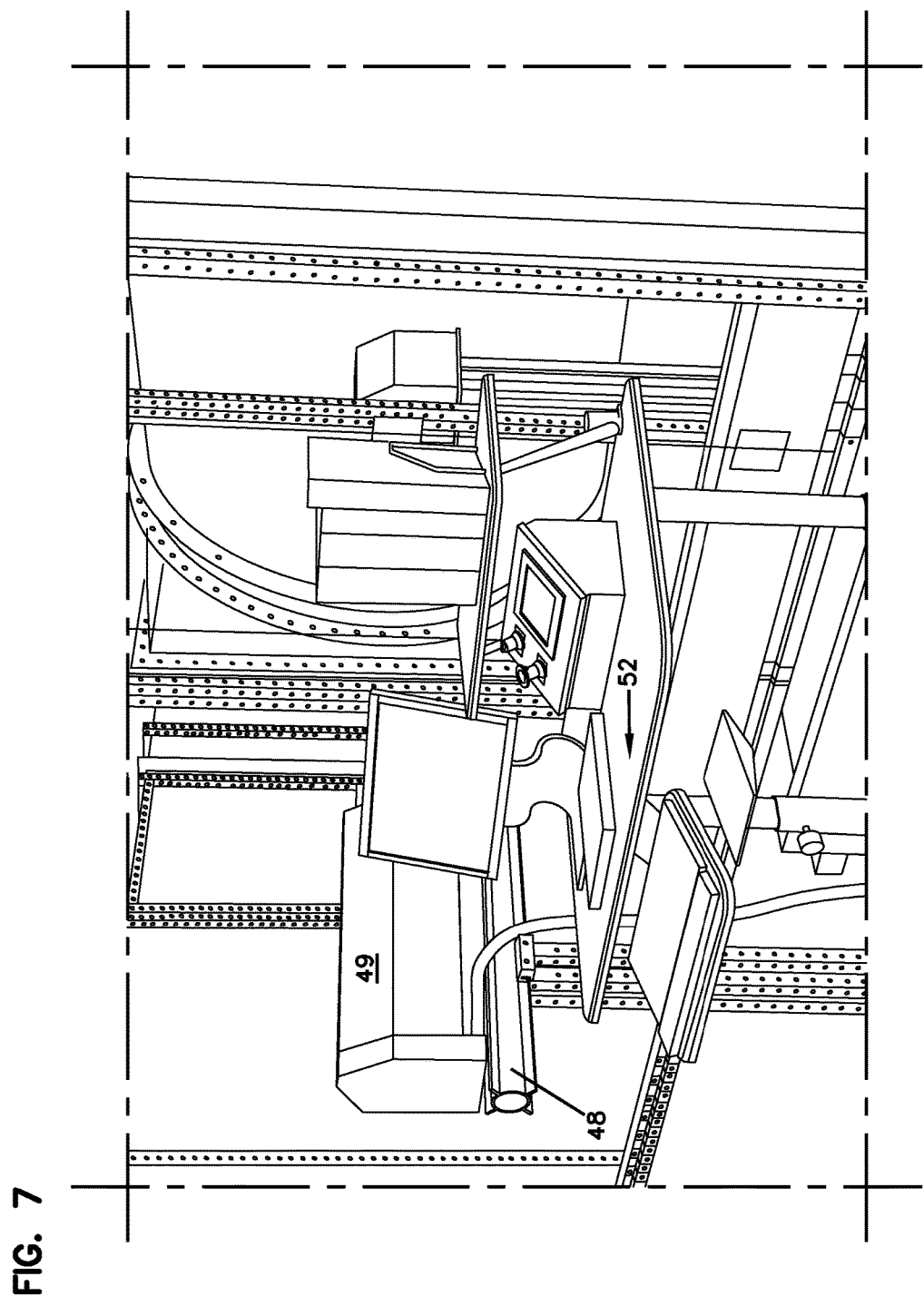
FIG. 7 is a view of an operating console that may be provided in connection with the wind tunnel device of FIG. 1.

As shown in FIG. 7, a computer 52 may be configured as an operating console for the wind tunnel device 10 and may be communicatively coupled thereto. The computer 52 may include a processor, a memory and a network connection. In some implementations, the computer 52 may be used to operate the traversing arm 43, the laser mount 48, the laser 49, a fluid delivery system for delivering fluid to the spray tips 25 and so on. For example, using the computer 52, an operator may adjust the position of the laser mount 48 and the laser 49 horizontally and vertically. This may protect the laser 49 from being handled while readjusting and repositioning the laser 49. In some implementations, the laser 49 may be operated using proprietary Sympatec software, WINDOX provided on the computer 52. In addition, the computer 52 may be configured to control the traversing arm 43 to lower and raise the spray tip 25 joined thereto. A traversing arm motor (not shown) may also be operated using software on the computer 52.

Figure 4:
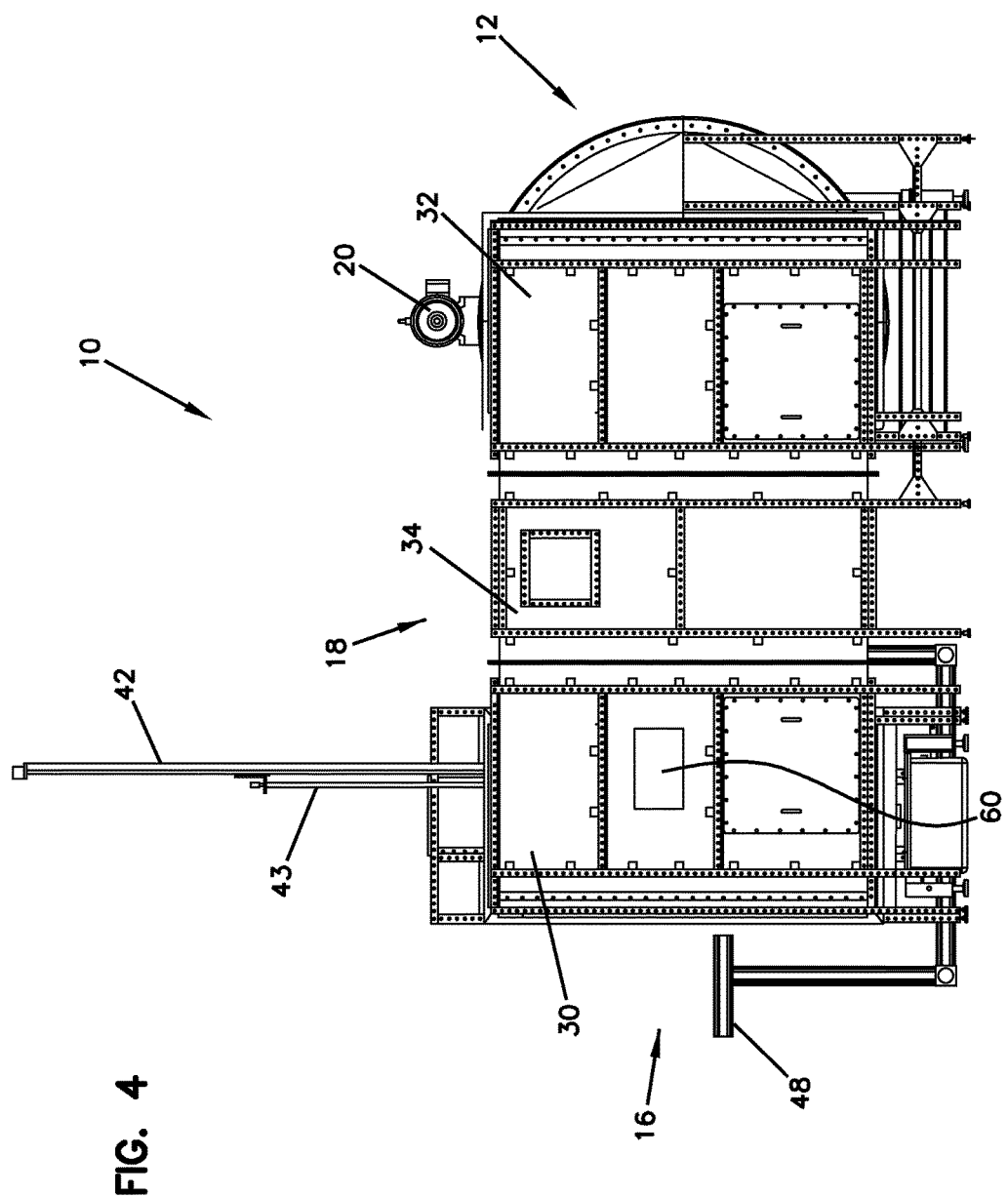
FIG. 4 is a right side view of the wind tunnel device of FIG. 1.

As shown in FIGS. 1 and 4, a control box 60 is mounted to the exterior of the wind tunnel device 10 and may be used to control the wind speed and a waste pump (not shown). The control box 60 may be operated using the computer 52 or may be operated separately therefrom.

As shown in FIGS. 1, 4 and 5, the third section 18 of the wind tunnel device 10 may include a third corner 30 and a fourth corner 32 connected by a second middle section 34. As shown in FIG. 5, the third corner 30, the fourth corner 32, and the second middle section 36 may define another side of the generally rectangular shape of the wind tunnel device 10. A portion of the tunnel 19 is formed within the volume enclosed by the third section 18. Similar to the first and second corners, each of the third and fourth corners 30 and 32 may include turning vanes 29. The third section 18 provides a connection between the fan 12 and the second section 16 to enable airflow to be re-circulated within the wind tunnel device 10. In some implementations, an exhaust system may be joined to the third section 18 to provide for safe removal of vapors or other contents in the airflow prior to re-circulating the airflow to the fan 12.

The wind tunnel device 10 disclosed herein provides several advantages over prior approaches. Because the device 10 is configured to re-circulate airflow, ambient air (e.g., air from an external environment in varying climates) need not be pumped into the device 10 from external sources, or at least a reduced amount of air is pumped into the device. For example, during summer and winter months when ambient temperatures are warm or cold, air within the device 10 may be reused, which avoid cooling and heating airflow prior to its introduction into the device 10. A further advantage provided by the device 10 is the ability to provide the laser in a separate environment from the interior of the device. This prevents the laser from fouling from spray particulates. In addition, because the laser may be mounted to the laser mount 48, the laser may be moved to multiple positions, which is in contrast to prior approaches in which lasers were statically mounted within a chemical hood. Yet another advantage provided by the device 10 is the ability to move the spray tip 25 within the device, including use of wide angle spray tips (110 to 140°) without fouling the test section. This differs from prior approaches in which the spray tip is mounted in one position, which may be problematic for leveling. Another advantage of the device is that the fully enclosed test chamber, facilitated by the optically clear glass, allows safe testing of active pesticide products.

Implementation of Use

In one implementation of use, the fan 12 may be operated by the motor 20 to force air through the tunnel 19 defined by the wind tunnel device 10. A spray tip 25 is attached to the traversing arm 43 of the test section 38. A conduit system adapted to transport fluids delivers fluid to the spray tip 25 to be sprayed therethrough. In some implementations, fluid may be forced to travel through the conduit system using an air compressor, pumps and so on. For example, the fluid to be delivered to the spray tip 25 may be tank mixed and pressurized within the tank, the conduit system or both. The conduit system may be coupled to a flow meter in order to measure the flow rate and pressure of the fluid passing therethrough prior to exiting the spray tip 25. In general, the spray tip 25 configuration determines the flow rate and the pressure of the exiting spray. The use of a flow meter provides confirmation that the fluid passing through the conduit system is moving properly, or so that any pressure drops may be accounted for when analyzing the spray exiting the spray tip 25. This enables the user to comply with ASAE/ANSI S572.1 test standard for quality control and size classification of agricultural nozzles, which may vary in quality when purchased from the manufacturer.

Using a computer 52, the traversing arm 43 is vertically lowered and raised within the first portion 39 of the test section 38 so that that spray tip 25 travels from the first end 38a of the test section 38 to the second end 38b of the test section 38. A fluid, such as an herbicide, is sprayed and the airflow passes the spray tip 25 at between 1 and 14 miles per hour. The spray tip 25 delivers spray at about a 110° spray angle, which may exit the spray tip in a vertical orientation. However, the spray angle delivered may exceed 140°, for example, depending on the spray tip and fluid sprayed therefrom.

The airflow carries spray particulates from the spray tip 25 into the second portion 44 of the test section 38 with the first and second expansion cutouts 45, 46. The expansion cutouts 45, 46 of the second portion 44 may substantially prevent droplets from forming on the ceiling above the space covered by the laser 49, and the expansion cutout 46 prevents droplets from bouncing off the floor and into the space covered by the laser 49. In some cases, the spray area may be larger than the second portion 44 of the test section 38 with the first and second expansion cutouts 45, 46, and may impinge upon the test section floor and ceiling but the particulates may be collected in a drip pan and channeled away from the test section. Prior to measurement of the spray particulates, the computer 52 is used to position the laser 49. The computer 52 is used to collect readings and determine particle size, which may then be analyzed. In some embodiments, the analysis may be used to classify the spray particle size as "Very Fine," "Fine," "Medium," "Coarse," and "Very Coarse."

The spray particulate measurements primarily may be taken while traversing the arm vertically up or down. Generally, for full-pattern analysis, the spray pattern measured during the run must clear the laser measurement area, prior to and after the run. The laser analysis may be triggered by the spray entering the test area and stopped when the spray exits the test area.

The spray can also be measured from a static position in a variety of orientations for other types of analysis. The wind tunnel device 100 provided herein is particularly useful for identifying spray particulates of various sizes, including particulates having a size limit of less than 150 μm and less than 105 μm.

The wind tunnel device 10 provided herein, with the laser mount 48 proximate the glass sections 50 of the second portion 44, along with the expansion cutouts 45, 46, may enable the device 10 to deliver airflow past the spray tip 25 at a speed of between about 1 and 14 miles per hour, which corresponds to low testing speeds. Using low testing speeds, the laser 49 may accurately detect the particle sizes of the spray particulates within the testing region.

In addition, the results of the laser 49 analysis may provide accurate results because the expansion cutouts 45, 46 may prevent errant drops from passing through the path of the laser, described above.

Providing glass sections 50 proximate the laser mount 48 enables the laser 49 to analyze the spray particulates without the particulates contacting the laser 49. Users of the wind tunnel device 10 are also protected from exposure to the spray particulates due to the enclosed space formed by the series of joined segments forming the wind tunnel device 10.

The cyclical or rectangular shape of the wind tunnel device 10 further provides a system that re-circulates airflow, as described above. The re-circulated airflow entering the fan 12 may be clean using the spray particle scrubber 51 positioned downstream from the testing region 44 and upstream from the fan 12.

The following Example Embodiment provides an implementation in which the wind tunnel device 10 is used to analyze spray particulates from various spray tips; however, this Example Embodiment should not be construed as limiting.

Example Embodiment

In a particular embodiment, a wind tunnel device designed as low speed wind tunnel provided wind speeds from 1 to 14 miles per hour at the spray tip and included a laser analyzer, i.e., a Sympatec Helos Vario-KR laser diffraction particle size analyzer with an R7 lens, mounted on an automated adjustable base that moved the laser from 0-18 inches from the spray tip. The wind tunnel device was a cyclical closed system with a downstream spray mist extractor removing 99.7% of all spray particles down stream of the test section. The area used for spray particle measurements was 6 feet high by 3 feet wide with upper and lower expansion areas that allow for traversing of up to 140° angle spray tips. The study observed the percentage of droplets within a size limit of less than 150 µm and less than 105 µm. Droplets sized below these thresholds are generally undesirable in spray applications due to their potential to contribute to spray drift.

In this example, two spray tips were analyzed and a drift reducer was also analyzed using the spray tips. The tests were conducted with the spray tips traversed at the bottom of an aerodynamic arm joined to the cabinet of the wind tunnel device. The wind speed, spray pressure, traversing arm, and laser operation were controlled by a control panel operated by a user. The waste water was removed from under the extractor by an enclosed system. The water is pumped from the enclosed container into shuttles which are then shipped away for disposal.

The results of spray particulates produced by two different spray tips, spray tip 1 (XR11002) and spray tip 2 (AIXR11004) are provided in Table 1 below.

TABLE 1

Examples of Spray Particle Analysis
Water Compared to Herbicide Formula Through Two Spray Tips @ 40PSI

| Treatment | % particles < 105 µm | % particles < 150 µm | Volume Median Diameter (VMD)* |
|---|---|---|---|
| Spray tip 1 (XR11002) | | | |
| Water | 19.9 | 41.4 | 168.7 |
| Glyphosate + AMS | 22.8 | 46 | 158.4 |
| Spray Tip 2 (AIXR11004) | | | |
| Water | 1.3 | 3.8 | 494.4 |
| Glyphosate + AMS | 2.7 | 7.6 | 387.6 |

*VMD = Half of spray volume is smaller and half the spray volume is larger than this number Table 1 illustrates the use of the wind tunnel device for testing the two different spray tips, which results in the detection of a large difference for the production of droplets smaller than 150 µm. Spray tip 1, XR11002 (XR TeeJet Extended Range Flat Spray Tip), spraying water and Glyphosate+AMS resulted in over 40 percent of the droplets having a size of less than 150 µm and about 20 percent of the droplets having a size of less than 105 µm. Spray tip 2, AIXR11004 (AIXR TeeJet Spray Tip), spraying water resulted in 3.8 percent of the droplets having a size of less than 150 µm and about 1.3 percent of the droplets having a size of less than 105 µm. For the same spray tip, spraying Glyphosate+AMS resulted in 7.6 percent of the droplets having a size less than 150 µm and 2.7 percent of the droplets having a size of less than 105 µm.

The results of herbicide spray particulates produced without and with a drift reducer (AG2013) using two different spray tips, spray tip 1 (XR11002) and spray tip 2 (AIXR11004) are provided in Table 2 below.

TABLE 2

Examples of Drift Reduction Adjuvant Reducing % of Fines in a Spray Mixture

| Treatment | % particulates < 105 µm | % particulates < 150 µm | Volume Median Diameter (VMD)* |
|---|---|---|---|
| Spray tip 1 (XR11002) | | | |
| Glyphosate + AMS (control) | 22.8 | 46 | 158.4 |
| Glyphosate + AMS + AG02013 | 13.2 | 34 | 182.1 |
| Spray Tip 2 (AIXR11004) | | | |
| Glyphosate + AMS (control) | 2.7 | 7.6 | 387.6 |
| Glyphosate + AMS + AG02013 | 0.7 | 2.8 | 459.4 |

*VMD = Half of spray volume is smaller and half the spray volume is larger than this number Table 2 illustrates the use of the wind tunnel device for testing the control herbicide and the herbicide with the drift control agent (AG2013) results in the detection of a large reduction of herbicide drift using the control agent.

Although the present disclosure provides references to preferred embodiments, persons skilled in the art will recognize that changes may be made in form and detail without departing from the spirit and scope of the invention.

The invention claimed is:

1. A wind tunnel device comprising:
    a testing region comprising:
        a first portion carrying a spray tip configured to deliver a spray in the testing region; and a second portion adapted to receive the spray and accommodate an area covered by the spray, wherein the wind tunnel device is configured such that airflow from an airflow system carries the spray through the testing region, and wherein the wind tunnel device is configured such that the airflow exiting the testing region is re-circulated using the airflow system; and a traversing arm configured to receive the spray tip.

2. The device of claim 1, wherein the airflow is carried past the spray tip at between about 1 and about 20 miles per hour.

3. The device of claim 1, wherein the airflow system comprises a fan.

4. The device of claim 3, wherein the fan is controlled by a computer.

5. The device of claim 1, wherein the wind tunnel device further comprises an analyzer configured to analyze the spray particulates in the testing region.

6. The device of claim 5, wherein the analyzer comprises a laser.

7. The device of claim 6, further comprising a computer configured to control the laser.

8. The device of claim 1, further comprising a computer configured to control one or more of the traversing arm or a fluid delivery system fluidly coupled to the spray tip.

9. The device of claim 1, wherein at least a portion of the testing region comprises transparent sidewalls.

10. The device of claim 1, wherein the traversing arm is configured to interchangeably receive a plurality of spray tips.

11. The device of claim 1, wherein the testing region is adapted to accommodate a plurality of spray patterns.

12. The device of claim 11, wherein at least a portion of the testing region is enlarged relative to other portions of the wind tunnel device.

13. A method of analyzing spray particulates in a wind tunnel comprising:

using a spray tip received in a traversing arm to deliver a spray in a testing region, the testing region adapted to receive the spray;

analyzing the spray as airflow carries the spray through the testing region; and using an airflow system to re-circulate the airflow through an enclosed interior of the wind tunnel.

14. The method of claim 13, wherein the step of analyzing is performed by a laser.

15. The method of claim 13, further comprising using a computer to control one or more the traversing arm, a laser mount, a laser, or a fluid delivery system fluidly coupled to the spray tip.

16. The method of claim 13, wherein the airflow is carried past the arm at between about 1 and about 20 miles per hour.

17. A wind tunnel, comprising:

a traversing arm adapted to receive a spray tip and to traverse into an area defined by a testing region;

a first expansion attached to the testing region; and a second expansion attached to an opposite side of the testing region from the first expansion, wherein the first and second expansions enable spray particles from the spray tip to pass through the testing region.

18. The wind tunnel of claim 17, further comprising an analyzer.

19. The wind tunnel of claim 17, further comprising a fan.

* * * * *